United States Patent
Reinholdt-Nielsen

(10) Patent No.: US 10,136,843 B2
(45) Date of Patent: Nov. 27, 2018

(54) AUDIOLOGIC TEST APPARATUS, SYSTEM AND RELATED METHOD

(71) Applicant: Natus Medical Incorporated, San Carlos, CA (US)

(72) Inventor: Christian Reinholdt-Nielsen, Frederikssund (DK)

(73) Assignee: Natus Medical Incorporated, Pleasanton, CA (US)

( * ) Notice: Subject to any disclaimer, the term of this patent is extended or adjusted under 35 U.S.C. 154(b) by 180 days.

(21) Appl. No.: 14/261,331

(22) Filed: Apr. 24, 2014

(65) Prior Publication Data

US 2015/0305678 A1 Oct. 29, 2015

(30) Foreign Application Priority Data

Apr. 23, 2014 (DK) .................................. 2014 70234
Apr. 23, 2014 (EP) ..................................... 14165582

(51) Int. Cl.
*A61B 5/12* (2006.01)
*A61B 5/00* (2006.01)

(52) U.S. Cl.
CPC .............. *A61B 5/125* (2013.01); *A61B 5/126* (2013.01); *A61B 5/6843* (2013.01); *A61B 5/6817* (2013.01)

(58) Field of Classification Search
CPC ........... A61B 5/12; A61B 5/121; A61B 5/125; A61B 5/126; A61B 5/128; A61B 5/6815;
(Continued)

(56) References Cited

U.S. PATENT DOCUMENTS

| 4,237,905 A | 12/1980 | Keller et al. |
| 4,688,582 A | 8/1987 | Heller et al. |

(Continued)

FOREIGN PATENT DOCUMENTS

| CN | 1850002 A | 10/2006 |
| CN | 102813519 A | 12/2012 |
| WO | WO 98/06324 A1 | 2/1998 |

OTHER PUBLICATIONS

Second Technical Examination—Intention to Grant dated May 28, 2015, for related Danish Patent Application No. PA 2014 70234, 2 pages.

(Continued)

*Primary Examiner* — Adam J Eiseman
(74) *Attorney, Agent, or Firm* — Temmerman Law Office; Mathew J. Temmerman

(57) ABSTRACT

An audiologic test apparatus includes: a processing unit; a tone generator connected to the processing unit; and a probe interface for connecting the audiologic test apparatus to a test probe; the tone generator configured to provide a first electrical signal representative of a first signal with a first primary frequency component at a first primary frequency; wherein the processing unit is configured to: obtain a first response signal, determine if a first insertion criterion is satisfied, the first insertion criterion based on the first signal and the first response signal, and generate a signal to initiate an audiologic test if at least the first insertion criterion is satisfied; the tone generator configured to provide a second electrical signal representative of a second signal with a second primary frequency component at a second primary frequency during the audiologic test, the first primary frequency being lower than the second primary frequency.

19 Claims, 9 Drawing Sheets

(58) Field of Classification Search
CPC .... A61B 5/6816; A61B 5/6817; A61B 5/6843
See application file for complete search history.

(56) References Cited

U.S. PATENT DOCUMENTS

| | | | |
|---|---|---|---|
| 5,577,511 A | 11/1996 | Killion | |
| 5,825,894 A | 10/1998 | Shennib | |
| 6,231,521 B1* | 5/2001 | Zoth | A61B 5/121 |
| | | | 128/898 |
| 6,299,584 B1* | 10/2001 | Iseberg | A61B 5/12 |
| | | | 600/559 |
| 7,050,592 B1 | 5/2006 | Iseberg et al. | |
| 7,976,474 B2* | 7/2011 | Zoth | A61B 1/227 |
| | | | 600/559 |
| 2006/0204014 A1* | 9/2006 | Iseberg | A61B 5/121 |
| | | | 381/60 |
| 2007/0156063 A1* | 7/2007 | Zoth | A61B 5/121 |
| | | | 600/559 |
| 2008/0194984 A1* | 8/2008 | Keefe | A61B 5/121 |
| | | | 600/559 |
| 2010/0191144 A1 | 7/2010 | Zoth et al. | |
| 2014/0114209 A1* | 4/2014 | Lodwig | A61B 5/7228 |
| | | | 600/559 |

OTHER PUBLICATIONS

First Technical Examination dated Nov. 10, 2014, for related Danish Patent Application No. PA 2014 70234, 4 pages.
Extended European Search Report dated Jul. 9, 2014 for related EP Patent Application No. EP 14165582.9, 6 pages.

* cited by examiner

AUDIOLOGIC TEST APPARATUS, SYSTEM AND RELATED METHOD

RELATED APPLICATION DATA

This application claims priority to and the benefit of Danish Patent Application No. PA 2014 70234, filed on Apr. 23, 2014, pending, and European Patent Application No. 14165582.9, filed on Apr. 23, 2014, pending. The entire disclosures of both of the above applications are expressly incorporated by reference herein.

FIELD

The present disclosure relates to a method, a system and an apparatus for initiating and/or performing an audiologic test, such as tympanometry and/or an otoacoustic emission test, in an ear canal of a person. In particular, an audiologic test apparatus, system and method for performing an audiologic test is disclosed. The audiologic test may comprise a tympanometric and/or an otoacoustic emission test.

BACKGROUND

Audiologic tests, such as tympanometry and/or an otoacoustic emission test, examines the condition of the middle ear, mobility of the tympanic membrane, and/or the conduction bones by creating variations of pressure in the ear canal. In order to modify the pressure, a probe is inserted into the ear canal creating an air tight seal of the ear canal.

Audiologic tests are conventionally performed by transmitting a continuous tone with a primary frequency component at a primary frequency of 226 Hz towards the tympanic membrane and measuring via a microphone the signal reflected by the tympanic membrane. The choice of 226 Hz is a de facto standard in performing a tympanometry in adults. In small children a tympanometry is occasionally performed with a tone with a primary frequency component at a primary frequency about 1,000 Hz.

Conventionally apparatuses configured to perform audiologic tests incorporate measures to automatically detect if the probe is inserted into the ear. This is conventionally achieved by transmitting, through the test probe, the test tone, e.g. 226 Hz, whenever the apparatus is switched on. The microphone detects a reflection of the test tone, and the reflection is an indicator that the test probe is inserted into an ear canal. However, the reflection may indicate that the test probe is inserted into an ear canal, even if an air tight seal is not created. Hence, the apparatus may activate a pump to increase/decrease pressure even if the test probe is not correctly positioned in or at the ear canal.

SUMMARY

Despite the known solutions there is still a need for a system, apparatus and/or a method which decrease the risk of falsely initiating an audiologic test.

Accordingly, an audiologic test apparatus for performing an audiologic test in an ear canal, is provided. The audiologic test apparatus comprises a housing, a processing unit, a tone generator connected to the processing unit, and a probe interface for connecting the audiologic test apparatus to a test probe. The apparatus is configured to: generate by the tone generator a first electrical signal representative of a first signal with a first primary frequency component at a first primary frequency; receive a first response signal; determine if a first insertion criterion is satisfied, wherein the first insertion criterion is based on the first signal and the first response signal; and initiate the audiologic test if at least the first insertion criterion is satisfied. The audiologic test comprises generating a second electrical signal representative of a second signal with a second primary frequency component at a second primary frequency. The first primary frequency is lower than the second primary frequency.

Also disclosed is an audiologic test system for performing an audiologic test, the audiologic test system comprising: an audiologic test apparatus, such as the disclosed audiologic test apparatus, the audiologic test apparatus comprising a processing unit; a test probe with a first part for insertion into an ear canal, the test probe being connected to the audiologic test apparatus; a first speaker; and a first microphone. The audiologic test system is configured to: generate a first signal with a first primary frequency component at a first primary frequency; receive a first response signal; determine if a first insertion criterion is satisfied, wherein the first insertion criterion is based on the first signal and the first response signal; and initiate the audiologic test if at least the first insertion criterion is satisfied. The audiologic test comprises generating a second signal with a second primary frequency component at a second primary frequency. The first primary frequency is lower than the second primary frequency.

Also disclosed is a method for performing and/or initiating an audiologic test. The method may comprise performing one or more insertion tests including a first insertion test and/or a second insertion test, e.g. before and/or during the audiologic test. The method may comprise, e.g. as a part of the first insertion test, generating a first signal with a first primary frequency component at a first frequency; detecting a first response signal; determining if a first insertion criterion is satisfied, wherein the first insertion criterion is based on the first signal and the first response signal. The method may comprise initiating the audiologic test if at least the first insertion criterion is satisfied and/or if one or more insertion tests are passed. The audiologic test comprises generating a second signal with a second primary frequency component at a second primary frequency. The first primary frequency is lower than the second primary frequency.

The disclosed apparatus, system and method provide improved reliability of automation in audiologic test apparatuses and/or systems. The risk of activating unnecessary steps and/or unnecessary activation of mechanical parts is reduced.

Furthermore, the disclosed apparatus, system and method advantageously provide for faster test procedures, e.g. unsuccessful attempts may be avoided.

An even further advantage of the disclosed apparatus, system and method is that wear of mechanical parts, such as the pump, is reduced, e.g. unnecessary activation of mechanical parts are reduced, thereby reducing mechanical wear.

The audiologic test apparatus and/or the audiologic test system may be configured to perform the disclosed method and/or any steps of the disclosed method.

The disclosed apparatus, system and/or method may be used in performing an audiologic test, e.g. a tympanometric test and/or an otoacoustic emission test.

An audiologic test apparatus for performing an audiologic test includes: a housing; a processing unit in the housing; a tone generator connected to the processing unit; and a probe interface for connecting the audiologic test apparatus to a test probe; wherein the tone generator is configured to provide a first electrical signal representative of a first signal with a first primary frequency component at a first primary frequency; wherein the processing unit is configured to:

obtain a first response signal, determine if a first insertion criterion is satisfied, wherein the first insertion criterion is based on the first signal and the first response signal, and generate a signal to initiate the audiologic test if at least the first insertion criterion is satisfied; and wherein the tone generator is configured to provide a second electrical signal representative of a second signal with a second primary frequency component at a second primary frequency during the audiologic test, the first primary frequency being lower than the second primary frequency.

Optionally, the first primary frequency component comprises a lower cut-off frequency of the tone generator.

Optionally, the audiologic test apparatus further includes a pump module connected to the processing unit, the pump module having a port in fluid communication with a pump port of the probe interface.

Optionally, the processing unit is configured to determine if a second insertion criterion is satisfied, wherein the second insertion criterion is based on a detected pressure response; and wherein the processing unit is configured to generate the signal to initiate the audiologic test if the first and second insertion criterion are satisfied.

An audiologic test system includes the audiologic test apparatus, a first speaker coupled to the tone generator, and a microphone coupled to the processing unit.

Optionally, the audiologic test system further includes a second speaker coupled to the tone generator.

Optionally, the first speaker and the microphone are parts of the audiologic test apparatus.

Optionally, the first speaker and the microphone are parts of the test probe.

An audiologic test system for performing an audiologic test includes: an audiologic test apparatus comprising a processing unit; a test probe with a first part for insertion into an ear canal, the test probe being connected to the audiologic test apparatus; a first speaker at the test probe or at the audiologic test apparatus; and a first microphone at the test probe or at the audiologic test apparatus; wherein the audiologic test apparatus is configured to: provide a first signal with a first primary frequency component at a first primary frequency, obtain a first response signal, determine if a first insertion criterion is satisfied, wherein the first insertion criterion is based on the first signal and the first response signal, and initiate the audiologic test if at least the first insertion criterion is satisfied; and wherein the audiologic test apparatus is configured to provide a second signal with a second primary frequency component at a second primary frequency during the audiologic test, the first primary frequency being lower than the second primary frequency.

Optionally, the first speaker is at the test probe, not at the audiologic test apparatus.

Optionally, the first speaker is at the audiologic test apparatus, not at the test probe.

Optionally, the first speaker is configured to provide the second signal.

Optionally, the audiologic test system further includes a second speaker for providing the second signal.

A method for performing an audiologic test includes: generating a first signal with a first primary frequency component at a first primary frequency; detecting a first response signal; determining if a first insertion criterion is satisfied, wherein the first insertion criterion is based on the first signal and the first response signal; initiating the audiologic test if at least the first insertion criterion is satisfied; and generating a second signal with a second primary frequency component at a second primary frequency during the audiologic test, the first primary frequency being lower than the second primary frequency.

Optionally, the method further includes: modifying a pressure if the first insertion criterion is satisfied; detecting a pressure response; and determining if a second insertion criterion is satisfied, wherein the second insertion criterion is based on the detected pressure response; and wherein the audiologic test is initiated if the first and second insertion criterion are satisfied.

Other aspects and features will be evident from reading the following detailed description.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
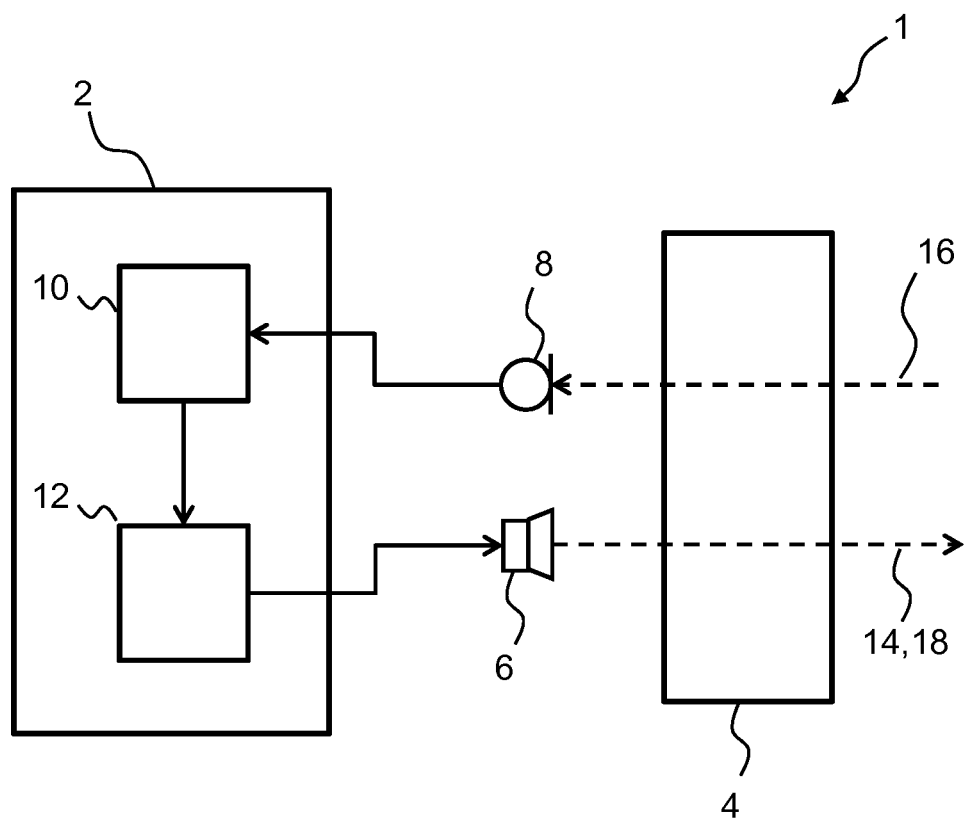
FIG. 1 schematically illustrates an exemplary audiologic test system.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

The first signal has a first primary frequency component at a first primary frequency, e.g. centered around or at a first primary frequency. The first signal may be a pure tone signal with the first primary frequency. The first signal may be an audio signal. The first primary frequency may be lower than 180 Hz, such as lower than 150 Hz, such as lower than 100 Hz, such as lower than 40 Hz. The first primary frequency may be larger than 5 Hz. The first primary frequency may be in the range from 15 Hz to 150 Hz, such as in the range from 30 Hz to 80 Hz. The first primary frequency may be 40 Hz or 20 Hz. The first signal may be transmitted whenever the apparatus and/or system is switched on or a test procedure is started.

The first signal may comprise a first secondary frequency component at a first secondary frequency, e.g. centered around or at a first secondary frequency. The first secondary frequency may be lower than 180 Hz, such as lower than 150 Hz, such as lower than 100 Hz, such as lower than 40 Hz. The first secondary frequency may be in the range from 15 Hz to 150 Hz, such as in the range from 30 Hz to 80 Hz. The first secondary frequency may be 60 Hz or 40 Hz.

The first response signal may at least partly be or comprise a reflection of the first signal. For example, the first response signal is a reflection of the first signal by a tympanic membrane in an ear canal.

The first insertion criterion is based on the first signal and the first response signal, e.g. one or more properties, such as time delay, power ratio, amplitude ratio, cross correlation, or admittance of the first signal and/or the first response signal. For example, the first insertion criterion may be satisfied if a predetermined degree of reflection of the first signal is detected in the first response signal.

The first insertion criterion may be based on a measured admittance based on the first signal and/or the first response signal. The measured admittance may be indicative of or equivalent to a volume. The first insertion criterion may be based on a threshold of the measured admittance and/or the volume indicative of or equivalent to the measured admittance.

Conventionally, an equivalent volume in ml is equal to the measured admittance in mmho when measured with a frequency of 226 Hz. The volume equivalent may be defined to be a volume in ml equal to the admittance in mmho measured with a frequency of 226 Hz. The volume equivalent measured with other frequencies may be:

$$V_{EQ} = Y \cdot \frac{\alpha}{f},$$

wherein $V_{EQ}$ is the volume equivalent in ml, Y is the admittance measured in mmho, f is the frequency measured in Hz, and $\alpha$ is a constant. The constant $\alpha$ can be set to 226 for the calculated $V_{EQ}$ to be comparable to a conventional volume equivalent measured with a frequency of 226.

The first insertion criterion may be satisfied if the volume equivalent is less than 10 ml.

The audiologic test may be initiated if the first insertion criterion is satisfied. Initiation of the audiologic test may depend on a plurality of insertion criteria or insertion tests, e.g. the first insertion criterion and a second insertion criterion. The audiologic test may be initiated automatically if the first insertion criterion is satisfied. The audiologic test comprises generating a second signal with a second primary frequency component at a second primary frequency, e.g. centered around or at a second primary frequency. The apparatus may be configured to stop or turn of generation of the first signal if the first insertion criterion is satisfied.

The second signal has a second primary frequency component at a second primary frequency, e.g. centered around or at a second primary frequency. The second signal may be an audio signal. The second primary frequency may be in the range from 190 Hz to 250 Hz, such as 200 Hz or 226 Hz, such as conventionally used for audiologic tests, such as tympanometry. Alternatively, the second primary frequency may be in the range from 950 Hz to 1050 Hz, such as conventionally used for audiologic tests of small children. The first primary frequency may be lower or substantially lower than the second primary frequency. For example, the difference between the first primary frequency and the second primary frequency may be at least 50 Hz, such as at least 100 Hz.

The first signal and/or the second signal may be a pure tone signal or substantially a pure tone signal, e.g. a signal consisting of a single frequency component or substantially a single frequency component.

Before initiating the audiologic test, the method may comprise initiating/performing a second insertion test, e.g. if the first criterion is satisfied or fulfilled or a first insertion test is passed. Before initiating the audiologic test, the method may comprise, e.g. as a part of the second insertion test, modifying pressure (in the ear canal) if the first insertion criterion is satisfied or the first insertion test is passed. The method may further comprise, e.g. as a part of the second insertion test, detecting a pressure response. Furthermore, the method may comprise, e.g. as a part of the second insertion test, determining if a second insertion criterion is satisfied. The second insertion criterion may be based on the pressure response and/or the pressure modification. The audiologic test may be initiated if the first and second insertion criterions are satisfied and/or if the first insertion test and the second insertion test are passed.

The audiologic test apparatus comprises a housing. The housing may enclose one or more components of the audiologic test apparatus, e.g. the processing unit. The audiologic test apparatus may comprise one or more interfaces, such as the probe interface, for communication between components enclosed in the housing and components and/or users external to the audiologic test apparatus. The housing may be a metal housing, a plastic housing and/or a combination of a metal and plastic housing.

The audiologic test apparatus comprises a processing unit. The processing unit may comprise a microprocessor, an analogue-to-digital converter (ADC), and/or a memory module. The processing unit may be configured to perform signal analysis of one or more input signals, such as the first response signal. The processing unit may be configured to provide one or more output signals, such as control signals. For example, the processing unit may provide a control signal to the tone generator, such as a first and/or second control signal, whereby the tone generator is instructed to generate an electrical signal, such as the first electrical signal and/or the second electrical signal.

The audiologic test system may comprise a tone generator. The tone generator of the test system may be a tone generator of the audiologic test apparatus. The tone generator may be configured to generate an electrical signal, such as the first electrical signal, or such as the second electrical signal. The electrical signal may be representative of a signal with a primary frequency component at a primary frequency, such as the first signal with the first primary frequency component at a first primary frequency, and/or such as the second signal with the second primary frequency component at the second primary frequency. The tone generator may be connected to one or more speakers, such as the first speaker and/or a second speaker, wherein the one or more speakers converts the electrical signal(s) of the tone generator to the signal represented by the electrical signal.

The audiologic test apparatus may comprise a probe interface. The probe interface may provide a possibility of connecting a probe to the audiologic test apparatus. The probe interface may comprise one or more electrical connectors and/or one or more fluid communication channels, such as a pump port. The one or more electrical connectors may provide electrical communication between components of the audiologic test apparatus and components of the probe. For example, the electrical connectors may provide electrical communication between the tone generator and a speaker, such as the first speaker, and/or between the processing unit and a microphone, such as the first microphone. The one or more fluid communication channels and/or pump ports may provide fluid communication between the probe and a pump module of the test apparatus, e.g. in order to adjust pressure in the ear canal of a test person.

The test probe may be connectable to the audiologic test apparatus. Alternatively and/or additionally, the test probe may be connected to the audiologic test apparatus.

The test probe may comprise one or more parts including a first part and/or a second part. A part of the test probe, such as the first part, may be configured for insertion into an ear canal. The test probe and/or the first part of the test probe may be adapted to receive a disposable and/or flexible tip. The disposable and/or flexible tip may be designed to perform an air tight seal of the ear canal. A disposable tip may prevent requirement of sterilizing the probe because the disposable tip may be sterile and disposed of after use. The tip may facilitate adaption of the test probe for different ear canal geometries/sizes.

The audiologic test system may comprise one or more speakers, such as the first speaker and/or a second speaker. The audiologic test apparatus may comprise one or more speakers, such as the first speaker and/or the second speaker. The test probe may comprise one or more speakers, such as the first speaker and/or the second speaker.

The first speaker and/or second speaker may be connected and/or connectable to the tone generator, e.g. via the probe interface. The first signal may be generated by the first speaker and/or the second speaker. The second signal may be generated by the first speaker and/or the second speaker. The first signal may be generated by the first speaker and the second signal may be generated by the second speaker.

The audiologic test apparatus may comprise a microphone, such as the first microphone. The test probe may comprise a microphone, such as the first microphone. The first microphone may be connected and/or connectable to the processing unit, e.g. via the probe interface.

The apparatus/system may comprise a display, such as an LCD display, such as an LED display, such as an OLED display. The apparatus, such as the housing of the apparatus, may comprise the display.

The first primary frequency component may be at a lower cut-off frequency of the tone generator. For example, the first primary frequency may be the lowest frequency that the tone generator can generate. It may be beneficial to use the lowest possible frequency for detecting enclosure of the probe/correct positioning of the test probe in the ear canal.

The audiologic test apparatus may comprise a pump module. The pump module may be connected to the processing unit. The pump module may have a port in fluid communication with the pump port of the probe interface. The audiologic test apparatus, e.g. the pump module, and/or the test probe may comprise a pressure sensor. The pressure sensor may be configured to measure the actual pressure in the ear canal.

The audiologic test may comprise modifying the pressure in the ear canal, and the pressure in the ear canal may be modified and/or sensed by the use of the pump module.

The apparatus and/or system may be configured to perform a second insertion test. The second insertion test may be based on generation and detection of pressure/pressure changes in the ear canal. The second insertion test may be a leakage test.

The apparatus and/or system may be configured to modify pressure if the first insertion criterion is satisfied. The apparatus and/or system may furthermore be configured to detect a pressure response. The apparatus and/or system may furthermore be configured to determine if a second insertion criterion is satisfied. The second insertion criterion may be based on the pressure response. The apparatus and/or system may furthermore be configured to initiate the audiologic test if the first and second insertion criterions are satisfied.

The pump module may be configured to modify the pressure if the first insertion criterion is satisfied. The pressure sensor may be configured to detect the pressure response. The processing unit may be configured to determine if the second insertion criterion is satisfied, e.g. the processing unit may be configured to analyze the pressure response to determine if the second insertion criterion is satisfied. The processing unit may furthermore initiate the audiologic test if the first and second insertion criterions are satisfied.

FIG. 1 schematically illustrates an exemplary audiologic test system 1 for performing an audiologic test. The audiologic test system 1 comprises an audiologic test apparatus 2, a test probe 4, a first speaker 6, and a first microphone 8. The audiologic test apparatus comprises a processing unit 10, and a tone generator 12 connected to the processing unit 10. The first microphone 8 is connected to the processing unit 10, and the first speaker is connected to the tone generator 12.

The audiologic test system 1 is configured to generate a first signal 14 with a first primary frequency component at a first primary frequency, and receive a first response signal 16. The audiologic test system 1 generates the first signal 14 by the first speaker 6 and transmits the first signal 14 via the test probe 4. The audiologic test system 1 receives the first response signal 16 by the first microphone 8 via the test probe 4.

The audiologic test system 1 is further configured to determine if a first insertion criterion is satisfied, wherein the first insertion criterion is based on the first signal 14 and the first response signal 16. The audiologic test system 1 is further configured to initiate the audiologic test if at least the first insertion criterion is satisfied. The audiologic test comprises that the audiologic test system 1 generates a second signal 18 with a second primary frequency component at a second primary frequency and measuring a reflection from e.g. a tympanic membrane in an ear canal. The audiologic test system 1 generates the second signal 18 by the first speaker 6 and transmits the second signal 18 via the test probe 4.

The first signal 14 and the second signal 18 differ at least by their primary frequencies at different primary frequencies. Hence, the first primary frequency is lower than the second primary frequency. For example, the first primary frequency may be lower than 180 Hz, such as lower than 120 Hz, such as lower than 80 Hz, such as lower than 50 Hz, such as lower than 40 Hz, such as 20 Hz. The second primary frequency may be in the range above approximately 200 Hz such as in the range between 190 Hz and 250 Hz, e.g. with second primary frequency between 200 Hz and 230 Hz, such as 200 Hz or 226 Hz or in the range of approximately 900 Hz-1100 Hz such as 1000 Hz. In an exemplary apparatus, the second primary frequency of second signal 18 may be chosen in the range of 180-250 Hz for persons to be tested aged approximately 6 months and above, and the second primary frequency of second signal 18 may be chosen in the range 950 Hz-1050 Hz for persons to be tested aged below approximately 6 months.

The first response signal 16 may at least partly be a reflection of the first signal 14. Analysis of the first response signal 16 may indicate that a probe part is inserted into a cavity, e.g. an ear canal. The first insertion criterion may, for example, be satisfied if a predetermined degree of reflection of the first signal 14 is found in the first response signal 16.

The first primary frequency component at low frequency provides an improved leakage detection than using a higher frequency, e.g. a frequency equivalent to the second primary frequency.

The determination of the first insertion criterion may be computed by the processing unit 10. The processing unit 10 may control the tone generator to generate the first and/or second signal via the first speaker 6. The processing unit may be configured to initiate the audiologic test if the at least first insertion criterion is satisfied.

Figure 2:
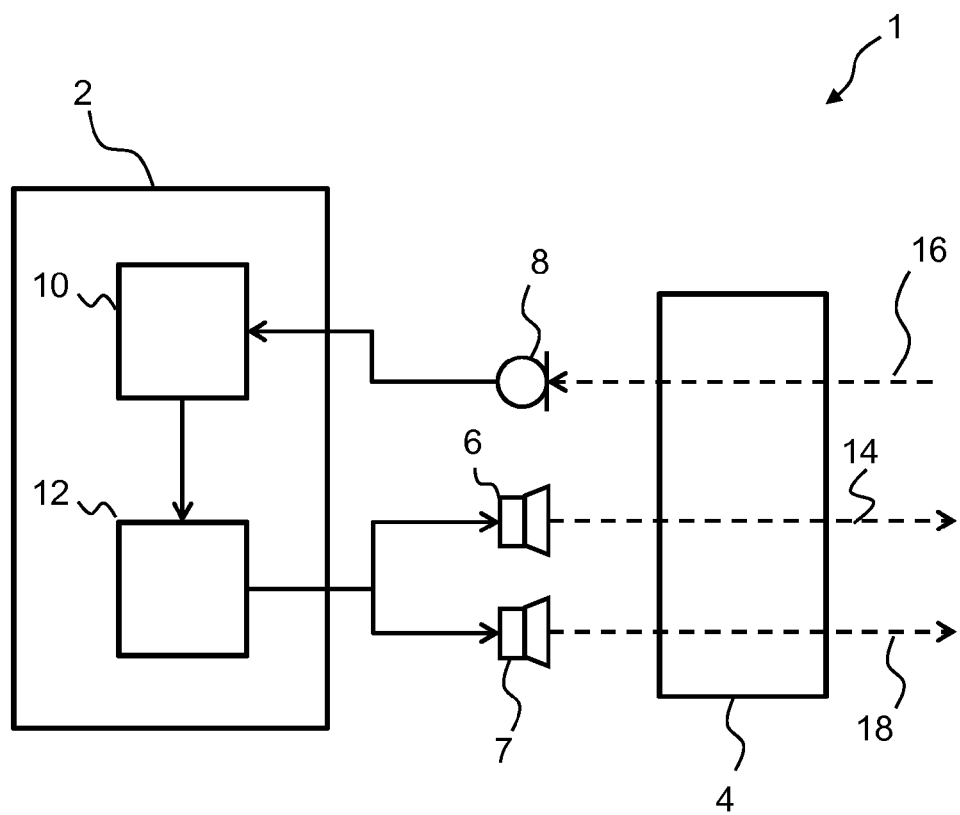
FIG. 2 schematically illustrates an exemplary audiologic test system.

FIG. 2 schematically illustrates an exemplary audiologic test system 1' for performing an audiologic test. The audiologic test system 1' is similar to the audiologic test system 1 of FIG. 1. However, the audiologic test system 1' comprises a second speaker 7, and the audiologic test system 1' is configured to generate the second signal 18 by the second speaker 7.

The first speaker 6 may be configured to generate the first signal 14 with the first primary frequency component at the first primary frequency, and the second speaker 7 may be configured to generate the second signal 18 with the second primary frequency component at the second primary frequency. In an exemplary system (not shown) the tone generator 12 may be omitted by utilizing designated first and second speakers that are specifically configured to transmit a signal having the first and second primary frequency component, respectively.

Figure 3:
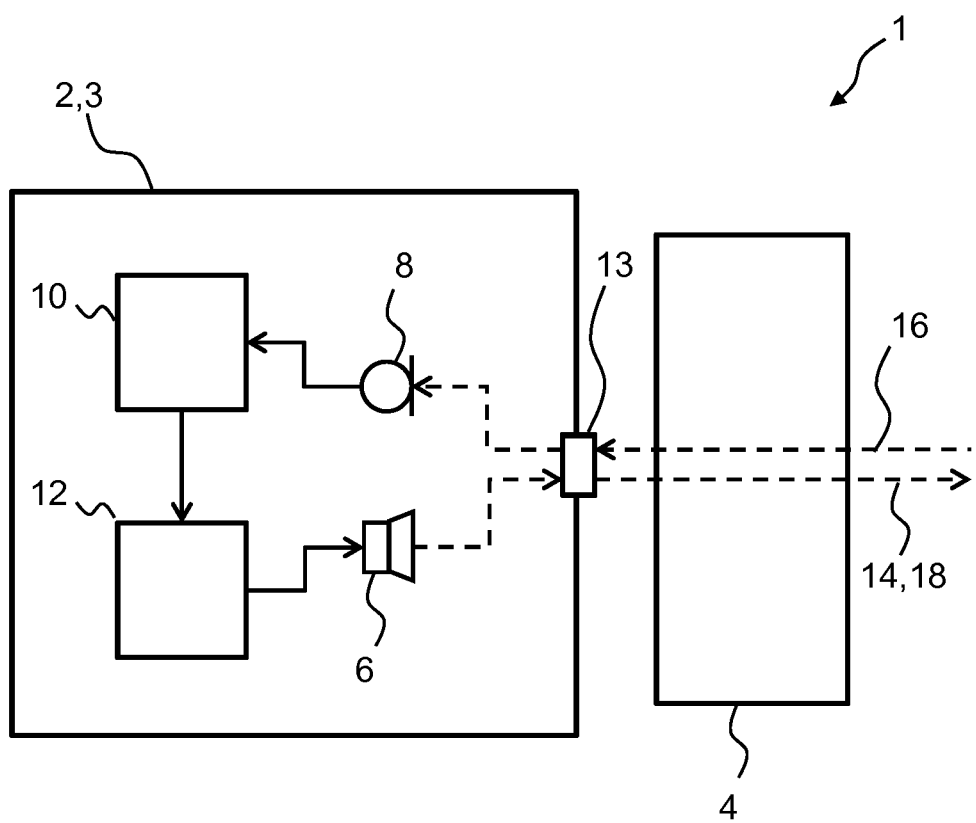
FIG. 3 schematically illustrates an exemplary audiologic test system.

FIG. 3 schematically illustrates an exemplary audiologic test system 1 for performing an audiologic test, wherein the audiologic test apparatus 2 comprises a housing 3, the first speaker 6 and the first microphone 8. The first speaker 6 and the first microphone 8 is comprised within the housing 3 of the audiologic test apparatus. Furthermore the audiologic test apparatus 2 comprises a probe interface 13 for connecting the test probe 4 to the audiologic test apparatus 2.

The first speaker 6 generates the first and/or second signal 14, 18. The first signal 14 and/or second signal 18 is transmitted through the probe interface 13 and the probe 4. Similarly, the first response signal 16 is received via the probe 4 and transmitted through the probe interface 13 to the microphone in the housing 3 of the audiologic test apparatus 2.

Figure 4:
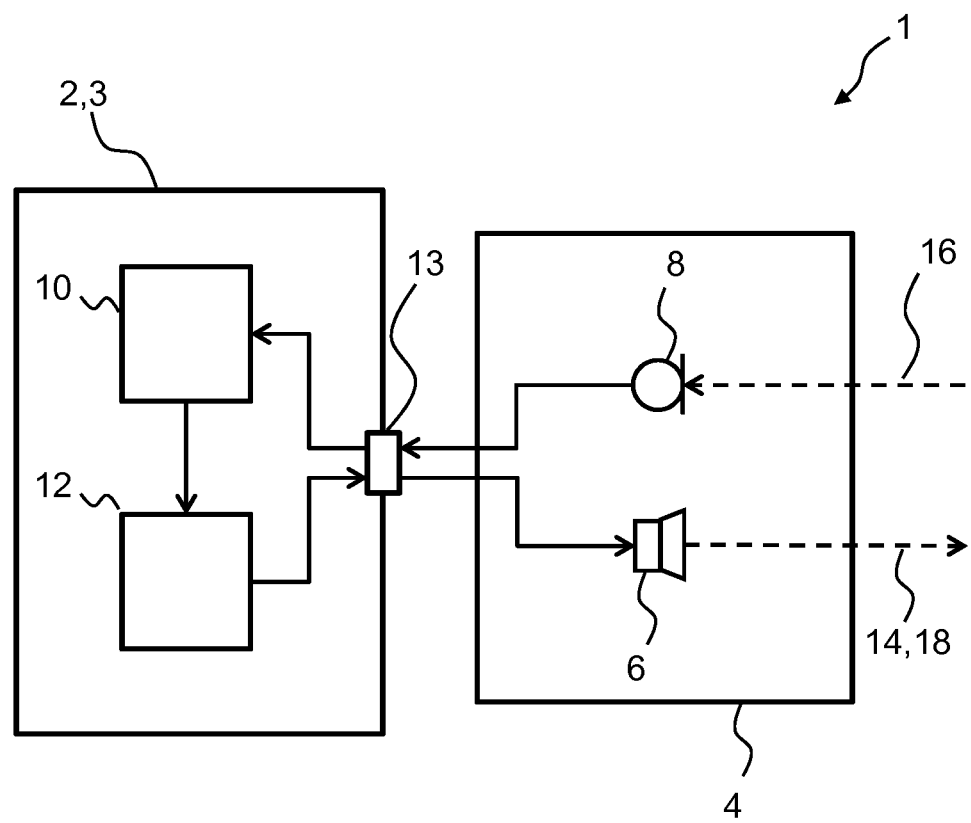
FIG. 4 schematically illustrates an exemplary audiologic test system.

FIG. 4 schematically illustrates an exemplary audiologic test system 1 for performing an audiologic test, wherein the test probe 4 comprises, the first speaker 6 and the first microphone 8. Furthermore the audiologic test apparatus 2 comprises a probe interface 13 for connecting the test probe 4 to the audiologic test apparatus 2.

A first and/or second electrical signal representative of the first and/or second signal 14, 18 is transmitted from the audiologic test apparatus 2 through the probe interface 13 to the first speaker 6 in the test probe 4. In response to receiving the first and/or second electrical signal, the first speaker 6 generates the first signal 14 and/or second signal 18 in the test probe 4. Similarly, the first response signal 16 is received by the first microphone 8 in the test probe. The first microphone 8 transmits a first electrical response signal representative of the first response signal 16 through the probe interface 13 to the audiologic test apparatus 2.

Figure 5:
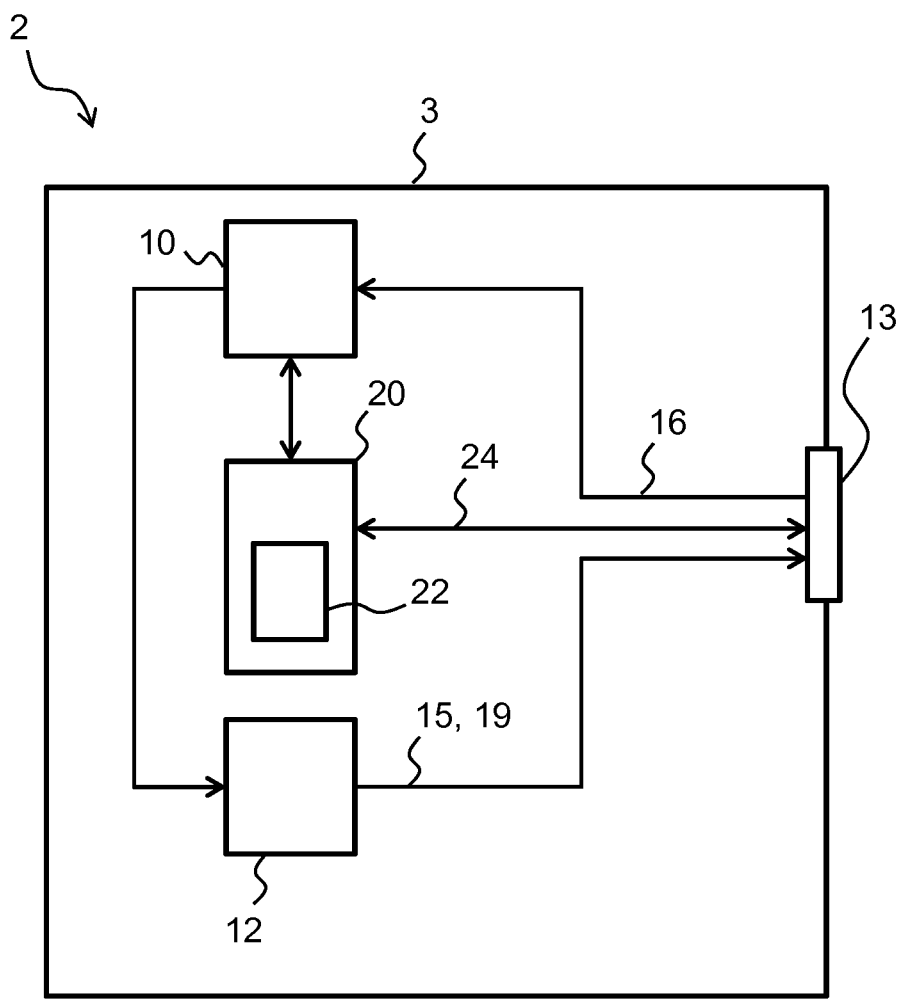
FIG. 5 schematically illustrates an exemplary audiologic test apparatus.

FIG. 5 schematically illustrates an exemplary audiologic test apparatus 2 for performing an audiologic test. The audiologic test apparatus 2 comprises a housing 3, a processing unit 10, and a tone generator 12.

The tone generator 12 generates a first electrical signal 15 representative of the first signal 14 (FIGS. 1-4). The first and/or second speaker 6, 7 (FIGS. 1-4) receives the first electrical signal 15 and generates the first signal 14. The tone generator furthermore generates a second electrical signal 19 representative of the second signal 18 (FIGS. 1-4). The first speaker 6 and/or the second speaker 7 receives the second electrical signal 19 and generates the second signal 18.

Generation of the first and second electrical signal 15, 19 may be simultaneous or differentiated in time. The second electrical signal 19 is at least generated during the audiologic test.

The exemplary audiologic test apparatus 2 as depicted in FIG. 5 furthermore comprises a pump module 20. The pump module 20 is in fluid connection 24 with a pump port of the probe interface 13. Hence, when a test probe is connected to the pump interface, and the probe is inserted into an ear canal (not shown), the pump module 20 may be in fluid connection with the ear canal.

The pump module 20 furthermore comprises a pressure sensor 22. The pressure sensor 22 is, in the depicted example, comprised within the pump module 20. However, the pressure sensor 22 may be positioned anywhere where it is able to detect the pressure in the ear canal. For example, in an alternative exemplary apparatus, the pressure sensor 22 is positioned in the probe interface 13.

A test probe 4 (FIG. 6) is connectable to the audiologic test apparatus via the probe interface 13. The probe interface 13 may comprise one or more electrical connectors and/or one or more fluid communication channels.

Figure 6:
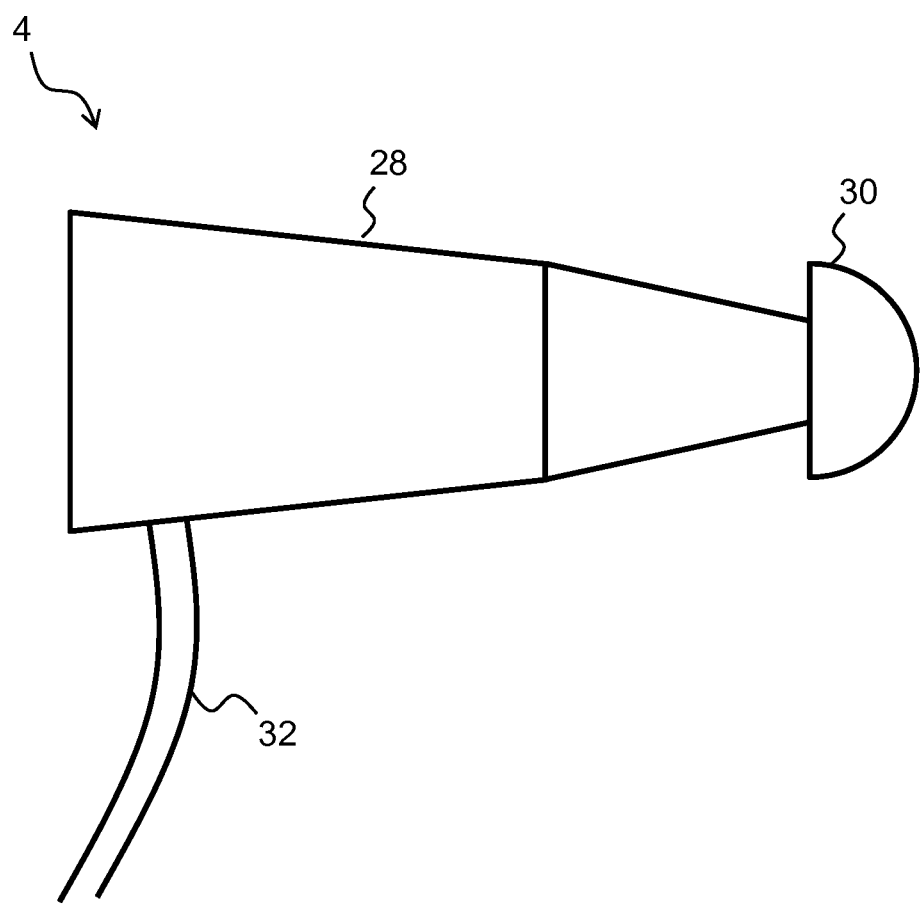
FIG. 6 schematically illustrates an exemplary test probe.

FIG. 6, schematically illustrates an exemplary test probe 4. The test probe 4 comprises a probe housing 28, and a first probe part 30. FIG. 6 furthermore illustrates a probe connector 32 for connecting the test probe 4 with an audiologic test apparatus. The first probe part 30 is adapted for insertion into an ear canal of a person (not shown).

Figure 7:
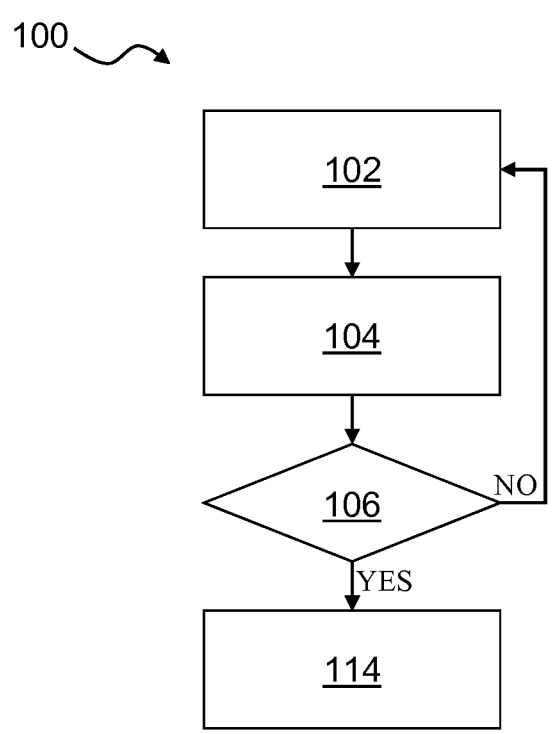
FIG. 7 is a flow diagram of a method for detecting insertion of a probe into an ear canal.

FIG. 7 is a flow diagram of a method 100 for detecting insertion of a probe into an enclosure, such as an ear canal. The method 100 comprises: generating 102 a first signal with a first primary frequency component at a first primary frequency; detecting 104 a first response signal; determining 106 if a first insertion criterion is satisfied; and initiating 114 an audiologic test.

The first insertion criterion may be based on the first signal generated 102 and the first response signal detected 104. The first insertion criterion may be indicative of whether the probe is inserted into a cavity, such as an ear canal. The first insertion criterion may be indicative of whether the probe provides a seal between the probe and the ear canal, such as between the probe and the wall of the ear canal. If determination 106 of the first insertion criterion yields that the first insertion criterion is satisfied, the method continues to initiation 114 of the audiologic test. If determination 106 of the first insertion criterion yields that the first insertion criterion is not satisfied, the method returns to the beginning of the method 100, i.e. generation 102 of the first signal. Furthermore, if the first insertion criterion is not satisfied, the method 100 may comprise signaling to reposition the probe, before returning to the beginning of the method 100. Signaling may be audible and/or visible signals to the operator.

The first signal has a first primary frequency component at a first primary frequency. The first primary frequency may be below 180 Hz, such as below 120 Hz, such as below 80 Hz, such as below 60 Hz, such as below 45 Hz.

The audiologic test comprises transmitting a second signal. The second signal has a second primary frequency component at a second primary frequency. The second primary frequency may be in the range of 190-250 Hz, such as in the range of 200-230 Hz, such as 220 or 226 Hz.

The first primary frequency of the first acoustic signal is lower than the second primary frequency of the second signal. The low first primary frequency provides a better detection of enclosure or sealing than using a higher frequency, e.g. a frequency equivalent to the second primary frequency. Thus, by detecting enclosure and/or leakage using a low frequency signal, such as the first signal having a first primary frequency component at a first primary frequency, the risk of falsely detecting an enclosure is decreased. Thereby, activation of the pump while unable to increase the pressure due to leaks or while the system is not ready for testing may be avoided.

Figure 8:
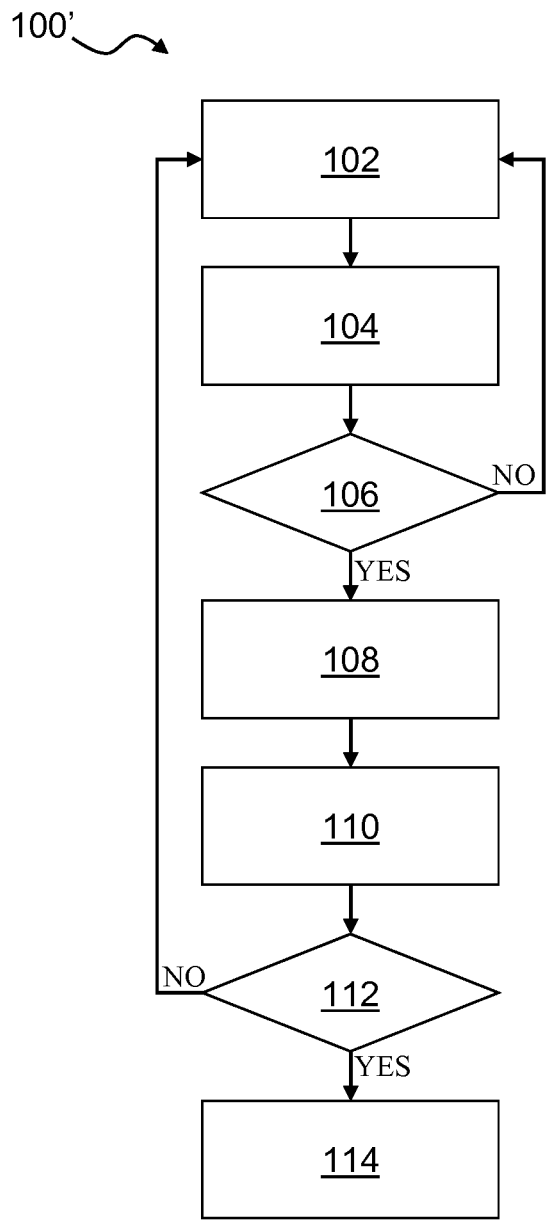
FIG. 8 is a flow diagram of a method for detecting insertion of a probe into an ear canal, and, FIG. 9 shows volume equivalents at different frequencies for a sealed cavity and a cavity with a leak

FIG. 8 is a flow diagram of a method 100' for detecting insertion of a probe into an enclosure, such as an ear canal. The method 100' comprises the same initial steps 102, 104, 106 as the method 100 shown in FIG. 7. The method 100' furthermore comprises modifying 108 the pressure in the ear canal, detecting 110 a pressure response, and determining 112 if a second insertion criterion is satisfied.

Modification 108 of the pressure may comprise increasing and/or decreasing the pressure. Detection 110 of the pressure response may provide information of the current pressure, e.g. relative to atmospheric pressure. Detection 110 of the pressure response provides information of whether the modification 108 of the pressure perform as intended, i.e. does the pressure rise and/or fall as expected? The pressure measurement may additionally be associated with the reflected signal, e.g. the first response signal 16 (FIGS. 1-5) to e.g. provide a reflex-measurement.

The second insertion criterion is based on the pressure response. The second insertion criterion is indicative of whether the probe is properly inserted into a cavity, such as an ear canal, and if an appropriate air tight seal is created. The second insertion criterion may be that the detected 110 pressure corresponds sufficiently to the modification 108 of the pressure. If determination 112 of the second insertion criterion yields that the second insertion criterion is satisfied, the method continues to initiation 114 of the audiologic test. If determination 112 of the second insertion criterion yields that the second insertion criterion is not satisfied, the method returns to the beginning of the method, i.e. generation 102 of the first signal. Alternatively, if determination 112 of the second insertion criterion yields that the second insertion criterion is not satisfied, the method may return to modification 108 of the pressure, e.g. because steps 102-106 have indicated a seal. Furthermore, if the second insertion criterion is not satisfied, the method 100 may comprise signaling to reposition the probe, before returning to the beginning of the method 100 and/or to modification 108 of the pressure. Signaling may be audible and/or visible signals to the operator.

Figure 9:
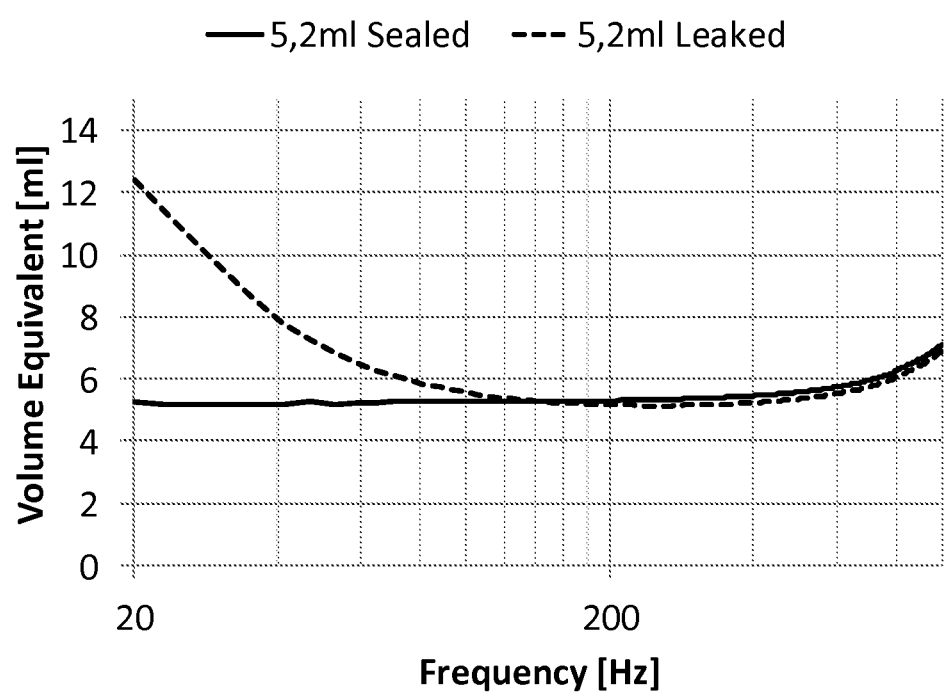

FIG. 9 shows test results for a test of detecting enclosure utilizing signals having different frequencies. The horizontal axis shows the frequency in Hz, such as the first primary frequency component of the first signal. The vertical axis shows the volume equivalent measured. The volume equivalent is derived from measuring admittance and applying the formula:

Volume equivalent [ml]=admittance [mmho]*226/frequency [Hz].

Two tests were performed with a cavity having a volume of 5.2 ml. The cavity had a small leak which could be opened or closed to imitate an air tight cavity and a leaking cavity.

For different frequencies, the solid line shows volume equivalents measured in a 5.2 ml sealed cavity, and the dashed line shows volume equivalents measured in a 5.2 ml cavity with a leak. The solid line shows that the volume equivalent is measured to be around 5.2 ml for all low frequencies, e.g. below 500 Hz, whereas the dashed line shows that for decreasing frequencies, the volume equivalent is increasing.

Comparing the results for the conventional used 226 Hz, the volume equivalent is measured to be the same in the sealed (solid line) and leaked (dashed line) cavity. This result implies that in this setup it cannot be determined from measuring using a first signal with a first primary frequency component of 226 Hz whether or not the cavity is sealed or leaked. However lowering the first primary frequency component of the first signal, e.g. to 20 Hz, the volume equivalent of the leaked cavity (dashed line) is measured to be approximately 12.5 ml. Hence, the risk of falsely detecting a sealed cavity where the cavity actually has a leakage is heavily reduced by the method and apparatus disclosed herein.

Exemplary audiologic test apparatuses, system and methods are disclosed in the following items:

Item 1. An audiologic test apparatus for performing an audiologic test in an ear canal, the audiologic test apparatus comprising:
 a housing,
 a processing unit,
 a tone generator connected to the processing unit, and
 a probe interface for connecting the audiologic test apparatus to a test probe,
wherein the apparatus is configured to:
 generate by the tone generator a first electrical signal representative of a first signal with a first primary frequency component at a first primary frequency;
 receive a first response signal;
 determine if a first insertion criterion is satisfied, wherein the first insertion criterion is based on the first signal and the first response signal; and
 initiate the audiologic test if at least the first insertion criterion is satisfied, the audiologic test comprising generating a second electrical signal representative of a second signal with a second primary frequency component at a second primary frequency;
wherein the first primary frequency is lower than the second primary frequency.

Item 2. Audiologic test apparatus according to item 1, wherein the first primary frequency component comprises a lower cut-off frequency of the tone generator i.e. wherein the first primary frequency is the lowest frequency that the tone generator may generate.

Item 3. Audiologic test apparatus according to any of items 1 or 2, the apparatus comprising a pump module connected to the processing unit and having a port in fluid communication with a pump port of the probe interface, wherein the audiologic test comprises modifying the pressure in the ear canal.

Item 4. Audiologic test apparatus according to item 3, wherein the pump module comprises a pressure sensor.

Item 5. Audiologic test apparatus according to any of the preceding items, wherein the apparatus is configured to
 modify pressure if the first insertion criterion is satisfied;
 detect a pressure response;

determine if a second insertion criterion is satisfied, wherein the second insertion criterion is based on the pressure response; and initiate the audiologic test if the first and second insertion criterion are satisfied.

Item 6. Audiologic test apparatus according to any of the preceding items, wherein the first primary frequency is lower than 180 Hz.

Item 7. An audiologic test system for performing an audiologic test, the audiologic test system comprising:
an audiologic test apparatus comprising a processing unit;
a test probe with a first part for insertion into an ear canal, the test probe being connected to the audiologic test apparatus;
a first speaker; and
a first microphone;
wherein the audiologic test system is configured to:
generate a first signal with a first primary frequency component at a first primary frequency;
receive a first response signal;
determine if a first insertion criterion is satisfied, wherein the first insertion criterion is based on the first signal and the first response signal; and
initiate the audiologic test if at least the first insertion criterion is satisfied, the audiologic test comprising generating a second signal with a second primary frequency component at a second primary frequency;
wherein the first primary frequency is lower than the second primary frequency.

Item 8. Audiologic test system according to item 7, wherein the test probe comprises the first speaker.

Item 9. Audiologic test system according to any of items 7-8, wherein the second signal is generated by the first speaker.

Item 10. Audiologic test system according to any of items 7-8, wherein the system comprises a second speaker, and wherein the second signal is generated by the second speaker.

Item 11. Audiologic test system according to item 10, wherein the test probe comprises the second speaker.

Item 12. A method for performing an audiologic test, the method comprising:
generating a first signal with a first primary frequency component at a first primary frequency;
detecting a first response signal;
determining if a first insertion criterion is satisfied, wherein the first insertion criterion is based on the first signal and the first response signal; and
initiating the audiologic test if at least the first insertion criterion is satisfied, the audiologic test comprising generating a second signal with a second primary frequency component at a second primary frequency;
wherein the first primary frequency is lower than the second primary frequency.

Item 13. Method according to item 12, wherein the method before initiating the audiologic test comprises:
modifying pressure if the first insertion criterion is satisfied;
detecting a pressure response;
determining if a second insertion criterion is satisfied, wherein the second insertion criterion is based on the pressure response; and
initiating the audiologic test if the first and second insertion criterion are satisfied.

Item 14. Method according to any of items 12 or 13, wherein the first primary frequency is lower than 180 Hz.

Item 15. Method according to any of items 12-14, wherein the first primary frequency is in the range from 15 Hz to 150 Hz.

Item 16. Method according to any of items 12-15, wherein the second primary frequency is in the range from 190 Hz to 250 Hz or in the range from 950 Hz to 1050 Hz.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

LIST OF REFERENCES 1 audiologic test system
2 audiologic test apparatus
3 housing
4 test probe
6 first speaker
7 second speaker
8 first microphone
10 processing unit
12 tone generator
13 probe interface
14 first signal
15 first electrical signal
16 first response signal
18 second signal
19 second electrical signal
20 pump module
22 pressure sensor
24 fluid communication
28 probe housing
30 probe first part
32 probe connector
100, 100' method
102 generating first signal
104 detecting response signal
106 determining first insertion criterion
108 modifying pressure
110 detecting pressure response
112 determining second insertion criterion
114 initiating audiologic test

The invention claimed is:

1. An audiologic test apparatus for performing an audiologic test, the audiologic test apparatus comprising:
a housing;
a processing unit in the housing;
a tone generator connected to the processing unit, the tone generator being instructed by the processing unit to generate a first electrical signal and a second electrical signal;
a probe interface for connecting the audiologic test apparatus to a test probe; and
a pump module having a pressure sensor connected to the processing unit;
wherein the first electrical signal is representative of a first signal with a first primary frequency component at a first primary frequency and the second electrical signal is representative of a second signal with a second primary frequency component at a second primary frequency, the first primary frequency being lower than the second primary frequency;
wherein the processing unit is configured to:
obtain a first response signal;
determine if a first insertion criterion is satisfied based on the first signal and the first response signal;
modify pressure in an ear canal;
detect a pressure response utilizing the pressure sensor;
determine if a second insertion criterion is satisfied; and
initiate the audiologic test to examine at least one part of an auditory system of a user;
wherein the processing unit is configured to receive an input generated using the pressure sensor and determines if the second insertion criterion is satisfied based on the input, the audiologic test includes generation of the second signal if the first and second insertion criterion are satisfied thereby indicating proper placement of the test probe in the ear canal to examine the at least one part of the auditory system of the user.

2. The audiologic test apparatus according to claim 1, wherein the first primary frequency component comprises a lower cut-off frequency of the tone generator.

3. The audiologic test apparatus according to claim 1, wherein the pump module having a port in fluid communication with a pump port of the probe interface.

4. The audiologic test apparatus according to claim 1, wherein the input is associated with the detected pressure response detected by the pressure sensor.

5. The audiologic test apparatus of claim 1, wherein a first speaker coupled to the tone generator, and a microphone coupled to the processing unit.

6. The audiologic test system of claim 5, further comprising a second speaker coupled to the tone generator.

7. The audiologic test system of claim 5, wherein the first speaker and the microphone are parts of the audiologic test apparatus.

8. The audiologic test apparatus of claim 5, wherein the first speaker and the microphone are parts of the test probe.

9. The audiologic test apparatus of claim 1, wherein the first primary frequency is below 100 Hz.

10. The audiologic test apparatus of claim 1, wherein the audiologic test comprises a tympanometric test, and wherein the second primary frequency that is higher than the first primary frequency is for the tympanometric test.

11. The audiologic test apparatus of claim 1, wherein the tone generator generates the first electrical signal at the first primary frequency and the second electrical signal at the second primary frequency utilizing a control signal from the processing unit.

12. An audiologic test system for performing an audiologic test, the audiologic test system comprising:
an audiologic test apparatus comprising:
a housing;
a processing unit in the housing;
a tone generator connected to the processing unit, the tone generator being instructed by the processing unit to generate a first electrical signal and a second electrical signal;
a probe interface for connecting the audiologic test apparatus to a test probe; and
a pump module having a pressure sensor connected to the processing unit;
a first speaker connected with the audiologic test apparatus; and
a first microphone connected with the audiologic test apparatus;
wherein the processing unit is configured to:
provide a first signal with a first primary frequency component at a first primary frequency through the first speaker, the first electrical signal is representative of the first signal;
obtain a first response signal from the probe interface through the first microphone;
determine if a first insertion criterion is satisfied based on the first signal and the first response signal;
modify pressure in an ear canal;
detect a pressure response utilizing the pressure sensor;
determine if a second insertion criterion is satisfied; and
initiate the audiologic test to examine at least one part of an auditory system of a user if the first insertion criteria and the second insertion criterion are satisfied, the audiologic test includes generation of the second signal with a second primary frequency component at a second primary frequency, the second electrical signal is representative of the second signal;
wherein the audiologic test apparatus is configured to receive an input generated using the pressure sensor and determines if the second insertion criterion is satisfied based on the input thereby indicating proper insertion of the test probe in the ear canal to examine the at least one part of the auditory system of the user.

13. The audiologic test system according to claim 12, wherein the first speaker is at the test probe.

14. The audiologic test system according to claim 12, wherein the first speaker is at the audiologic test apparatus, not at the test probe.

15. The audiologic test system according to claim 12, wherein the first speaker is configured to provide the second signal.

16. The audiologic test system according to claim 13, further comprising a second speaker for providing the second signal.

17. The audiologic test system of claim 12, wherein the first primary frequency is below 100 Hz.

18. The audiologic test system of claim 12, wherein the audiologic test comprises a tympanometric test, and wherein the second primary frequency that is higher than the first primary frequency is for the tympanometric test.

19. The audiologic test system of claim 12, wherein the tone generator generates the first electrical signal at the first primary frequency and the second electrical signal at the second primary frequency utilizing a control signal from the processing unit.

* * * * *